US008541241B2

(12) United States Patent
Wu et al.

(10) Patent No.: US 8,541,241 B2
(45) Date of Patent: Sep. 24, 2013

(54) FLUID-SPECIMEN COLLECTING AND TESTING DEVICE AND METHOD FOR RECORDING CHROMATOGRAPHIC ASSAY TEST RESULTS

(75) Inventors: John Wu, San Diego, CA (US); Jinying Liu, San Diego, CA (US); Chongyang Zhao, San Diego, CA (US)

(73) Assignee: Ameditech, Inc, Waltham, MA (US)

( * ) Notice: Subject to any disclaimer, the term of this patent is extended or adjusted under 35 U.S.C. 154(b) by 1391 days.

(21) Appl. No.: 11/542,731

(22) Filed: Oct. 3, 2006

(65) Prior Publication Data

US 2007/0026530 A1 Feb. 1, 2007

Related U.S. Application Data

(62) Division of application No. 09/862,235, filed on May 21, 2001, now Pat. No. 7,300,626.

(51) Int. Cl.
*G01N 33/48* (2006.01)

(52) U.S. Cl.
USPC ............. 436/165; 436/63; 436/164; 436/169; 422/400; 422/68.1; 422/417; 422/430

(58) Field of Classification Search
USPC .................. 422/400, 68.1, 417, 430; 436/63, 436/164, 165, 169
See application file for complete search history.

(56) References Cited

U.S. PATENT DOCUMENTS

| | | | | |
|---|---|---|---|---|
| 5,119,830 | A * | 6/1992 | Davis | 600/584 |
| 5,403,551 | A * | 4/1995 | Galloway et al. | 422/58 |
| 6,716,393 | B2 * | 4/2004 | Lappe et al. | 422/68.1 |
| 6,808,682 | B1 * | 10/2004 | Bates et al. | 422/58 |

* cited by examiner

*Primary Examiner* — Lyle Alexander

(74) *Attorney, Agent, or Firm* — Charmasson, Buchaca & Leach, LLP

(57) ABSTRACT

A fluid specimen testing device having a removable lid which carries at least one testing strip behind a transparent top viewing window. Testing is initiated by tilting the device into a stable sideways orientation to allow the specimen to contact the sampling pad portion of the strip. The device is adapted to provide stability in the upright, tilted and inverted orientations. A roll-inhibiting feature also acts as an indicator for proper roll positioning in the tilted configuration. The strips are also oriented in the lid so that they are substantially vertical when the device is in the tilted position thereby enhancing a condition for proper capillarity. The strip is carried close to the upper surface which allows it to be copied on a flat glass copier providing for more objective recordation of the test results.

12 Claims, 3 Drawing Sheets

FLUID-SPECIMEN COLLECTING AND TESTING DEVICE AND METHOD FOR RECORDING CHROMATOGRAPHIC ASSAY TEST RESULTS

PRIOR APPLICATION

This is a divisional of U.S. patent application Ser. No. 09/862,235 filed May 21, 2001 now U.S. Pat. No. 7,300,626.

FIELD OF THE INVENTION

This invention relates generally to fluid specimen containers, testing devices for conducting chromatographic reaction tests using assay testing strips for fluid specimens and more particularly to sealed receptacles for holding fluid specimens having testing capability.

BACKGROUND OF THE INVENTION

Fluid specimen jars or cups are commonly used to collect and test fluid specimens for the presence or absence of specific "indicators," which show the presence of specific chemicals, hormones, antibodies or antigens and are most commonly used for drug and pregnancy testing, among other types of assay tests.

Collecting and testing fluid specimens carries a measure of health risk for the person conducting the test and contamination risk to the specimen or testing media. Testing devices have previously required that a specimen be placed in a specimen cup and that a technician manually insert and submerge a portion of a testing strip into the specimen then, withdraw it to read the results. With the potential for contact with the sample by the technician and its associated health and contamination risks, a sealed receptacle for preventing contact is desirable. Various means have been proposed for further reducing the risk of contact as shown in U.S. Pat. No. 4,976,923 to Lipsky et al, and U.S. Pat. No. 5,429,804 to Sayles, which utilize a one-step testing device, with chromatographic testing strips mounted in their lids.

Others, as shown in U.S. Pat. No. 5,119,830 to Davis propose a test strip adhered to the floor of the lid, covered with a frangible surface which when punctured allows contact with the specimen when the device is inverted. A mylar-type sheet encasing the test strip and the frangible portion, defining the test space and preventing outside contact with the specimen during testing.

Other devices like U.S. Pat. No. 5,976,895 to Cipkowski, provide means for avoiding inversion. However, such devices are limited in that only a pre-determined amount of specimen can be tested. Overfilling encourages contact between specimen, and technician, either during insertion of the testing card, or when the technician opens the container to empty a portion of the contents. There can also be the difficulty of locating a proper place for discarding of the excess specimen. Also, if the maximum fluid level is exceeded, test results will not be reliable as the testing process may be adversely affected if the sample contacts the test strip higher than the sampling pad's limit line.

Often, medical device manufacturers, do not make products geared for use by the lay person, unless so targeted. Recently, the use of specimen testing devices by other than health care professionals has increased. Due to the fact that these tests are increasingly performed and evaluated by relatively unskilled technicians, the device needs to be relatively simple to operate to ensure adequate exposure of the test strip and provide accurate results. Devices that require inversion and subsequent righting of the container to conduct the test, involve certain measure of skill to provide adequate submersion of the test strips.

U.S. Pat. No. 5,403,551 to Galloway, requires inversion to an unspecified angle, making gauging adequate submersion of the test strips difficult and uncertain. Further, testing chambers that allow the flow of a fluid-specimen onto a test strip upon inversion, also allow the sample to escape upon righting, which can affect submersion of the test strip by trapping air-bubbles, which can inhibit the capillary movement of a specimen up a test strip. Since capillary action can be adversely affected by trapped air, and the position and orientation of the test strips. Devices which place the strips in a horizontal orientation, hinders capillary movement.

A "splash-shield" mechanism is shown by U.S. Pat. No. 5,429,804 to Sayles, to prevent secondary contact of the specimen with the test strip prior to the initial submersion to prevent premature testing of a specimen. In these devices, proper subjection of the test strip sampling pad to the specimen therefore requires a skill which may be beyond that of an inexperienced technician, resulting in unreliable and often inaccurate results. The splash-shield can also interfere with the submersion of the testing strip by trapping air-bubbles.

Since these tests are widely used in the medical industry, the workplace, athletic competitions and law enforcement. There is a need for being able to conduct various assay tests in large quantities. However, since testing materials are typically disposable, this can be costly. Testing devices are costly due to materials and difficulty in manufacturing, and are therefore not practical for use by certain organizations or institutions having limited resources.

Examples of complicated and thus costly testing devices are demonstrated by U.S. Pat. No. 5,403,551 to Galloway, et al and U.S. Pat. No. 5,976,895 to Cipkowski, both of which require multiple components, increasing materials and manufacturing cost. Both also require specially designed cartridges that are only compatible with a specific type of container.

Presently, test results are viewed by examining the test strip directly or through the testing device itself and manually recorded by a technician. Therefore, the results can be very subjective and without proof after the test strip has been saturated and/or discarded.

Therefore, there is a need to ensure proper testing, by allowing each strip to be in continuous, but controlled contact with the fluid sample, to orient the test strips in the most efficient position to maximize capillary movement of the specimen, and to vent or prevent air-bubbles, making the testing device easy to operate and produce more reliable results than previous testing devices.

The invention results from a need to reduce the above-mentioned deficiencies in the art.

SUMMARY OF THE INVENTION

The principal and secondary objects of this invention are to provide a cost-effective fluid specimen testing device that can provide reliable results by preventing premature testing of the fluid specimen and proper testing by complete and continuous submersion of the testing strips' sampling pads, and that can be easily used; and one in which results are recorded more objectively.

These and other valuable objects are achieved by a fluid specimen testing device having a removable lid, into which is mounted a testing strip behind a transparent top viewing window. Testing is initiated by tilting the device into a stable sideways orientation to allow the specimen to contact the sampling pad portion of the strip. The device is adapted to provide stability in the upright, tilted and inverted orientations. A roll-inhibiting feature also acts as an indicator for proper roll orientation in the tilted position. The strips are also oriented in the lid so that they are substantially vertical when the device is in the tilted position thereby enhancing a condition for proper capillarity. The strip is carried close to the lid's upper surface which allows it to be copied on a flat glass copier providing for more objective recordation of the test results. A specially adapted cavity allows enhanced uniformity in contact between multiple sampling pads and the specimen and discourages bubble formation and retention.

DESCRIPTION OF THE PREFERRED EMBODIMENT

Figure 1:
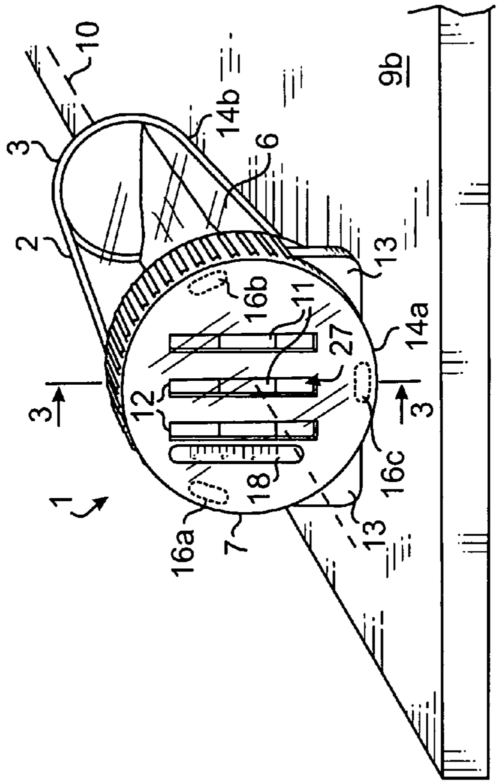
FIG. 1 is a perspective view of a first embodiment of a fluid-specimen device according to the invention in a test orientation.

Referring now to the drawing, there is shown in FIG. 1 through 4 a first embodiment of a fluid-specimen containing and testing device 1 having a cup portion 2 having a closed bottom end 3 and an opposite top opening 4 defining an inner chamber 5 for collecting a fluid specimen 6, and a lid 7 sized and shaped to seal the opening by corresponding threading 8. Other means well known in the art may be used to seal the lid to the cup.

Figure 2:
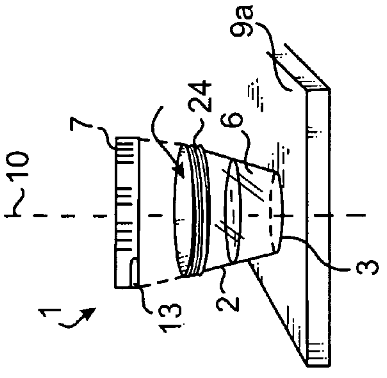
FIG. 2 is a perspective view of the device of FIG. 1 in an upright orientation.

As shown in FIG. 2, the bottom end 3 of the cup is flattened to allow it to rest on a substantially horizontal surface 9*a* in a stable, upright position and contain the specimen. The major axis 10 of the device is substantially vertical when the device is in an upright orientation.

The lid 7 has a substantially rigid, disk-shaped top portion 20 having a substantially planar outer, upper surface 17 and inner, lower surface 21. A substantially cylindrical flange 22 extends downward from the periphery of the top portion having inner threads 23 commensurate with corresponding threads 24 on outer upper periphery of the cup. The lid 7 is preferably made from substantially rigid, durable, fluid impermeable and non-reactive plastic material such as polycarbonate, polyethylene, polypropylene, or acrylic, and is adapted to carry a number of chromatographic assay test strips 11 within dedicated oblong pockets 12 behind transparent windows 27. An information carrying sticker 18 may be placed adjacent to the windows.

As shown in FIG. 1, the pockets 12 are positioned to orient the strips in a substantially vertical orientation when the device is in a tilted test orientation where the major axis 10 is substantially parallel to a horizontal support surface 9*b*. A pair of roll inhibiting ears 13 extend radially from the flange of the lid to help stabilize the device and thus help prevent the test strips from rolling beyond their optimum vertical test orientation. The ears also maintain the device at a predetermined and optimum test angle, and act as a readily perceived indicator of the proper roll position when the test is initiated. Other means well-known in the art may be employed to inhibit rolling motion. Pitch motion is prevented by top 14*a* and bottom 14*b* surfaces of the device respectively.

Figure 4:
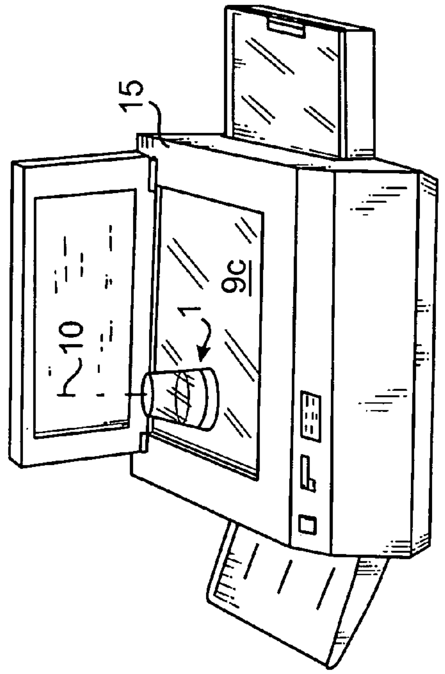
FIG. 4 is a perspective view of the device of FIG. 1 in an inverted orientation on a photocopier.

It is an important feature of the invention to provide for easy and more objective recordation of the test results. This is accomplished by placing the strips within the device in an orientation in which the results shown thereon may be recorded by an objective, automated reader such as a photocopier, scanner, camera or other well known or future reading apparatus. Means are provided to stabilize the device in an inverted orientation as shown in FIG. 4 when the device is resting on the horizontal glass surface 9*c* of a flat bed copier 15 where the major axis 10 is in a substantially inverted vertical orientation. In this embodiment three upper spaced apart portions 16*a*, 16*b*, 16*c* of the flat upper surface 17 of the lid form a plane and tripod support for the device in the inverted orientation. Additionally, the minimum distance D between the test strip and a photocopier contact surface CS is minimized so that precise recordation is accomplished. The distance will of course depend on the thickness of the viewing window, which will preferably range between about 1 and about 5 millimeters.

Figure 3:
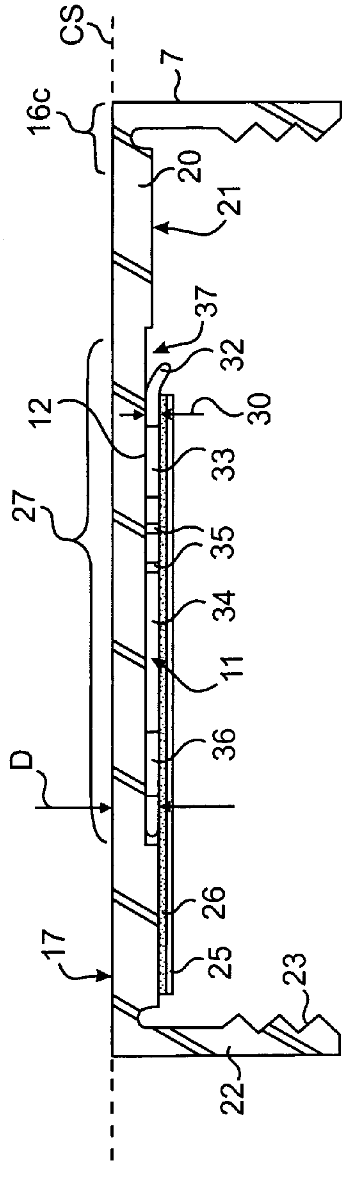
FIG. 3 is a cross-sectional view of the lid portion of the device of FIG. 1 taken along line 3-3.

Referring now to FIG. 3, each strip 11 is mounted within an oblong pocket 12 formed into the lid 7. The upper wall of the pocket is made from substantially transparent, fluid-resistant, non-reactive material to form a viewing window 27 between the pocket and the upper surface 17 of the lid allowing visual access to the strip. As shown in FIG. 3, the entire top portion and peripheral flange of the lid may be made from the same optically transparent material to reduce manufacturing costs.

The pocket 12 is formed by an oblong channel formed into the inner surface 21 and partially covered by a substantially planar backing 25 made of vinyl, foil, plastic, Teflon, or other fluid-impermeable and non-reactive sheet material having an attachment layer 26 of non-reactive, pressure sensitive adhesive. Such backings are commercially available from MBK Enterprises, Inc. of Chatsworth, Calif. Optionally, information may be printed on the adhesive side of the backing.

Partial covering of the channel thereby forms an aperture 30 through which extends the sampling pad portion 32 of the strip 11. The aperture is sized and shaped to encircle the strip thus preventing over-saturation of the test strip, which can adversely affect the testing process. The backing completely covers the rest of the channel so that the aperture is the only effective opening of the pocket. Therefore the strip and any trapped air helps prevent flow of fluid into the pocket. A depression 37 is sized and shaped to enhance uniformity of exposure between the sampling pad 32 and the specimen by allowing controlled contact to both sides of the sampling pad. The depression also forms a venting region allowing the escape of air-bubbles from near the sampling pad which would disrupt specimen-to-pad contact and reduce test accuracy.

The oblong channel is formed during injection molding of the lid to further save manufacturing costs. The pocket is shaped and dimensioned to closely envelop the test strip 11 to enhance the predictable movement of fluid up the strip by capillarity alone. The strip is one of any number of commonly available chemical assay devices well known in the art which, in general, are made up of various porous materials for carrying chemical reagents specifically selected to test for the adequate presence of a chemical in the specimen. One end of the strip is a sampling pad 32 for contacting the specimen. The rest of the strip is constructed to establish a predetermined flow of the specimen from the sampling pad up through a conjugate region 33, which conjugates the sought after chemical into one which is detectable, then through a membrane region 34 carrying test and control lines 35, and a terminal absorbent pad 36. Maintaining the substantially vertical orientation of the strips during testing helps prevent the fluid from contacting the strip above the sampling pad 32, which can result in inadequate conjugation or otherwise interfering with the proper test sequence.

Figure 6:
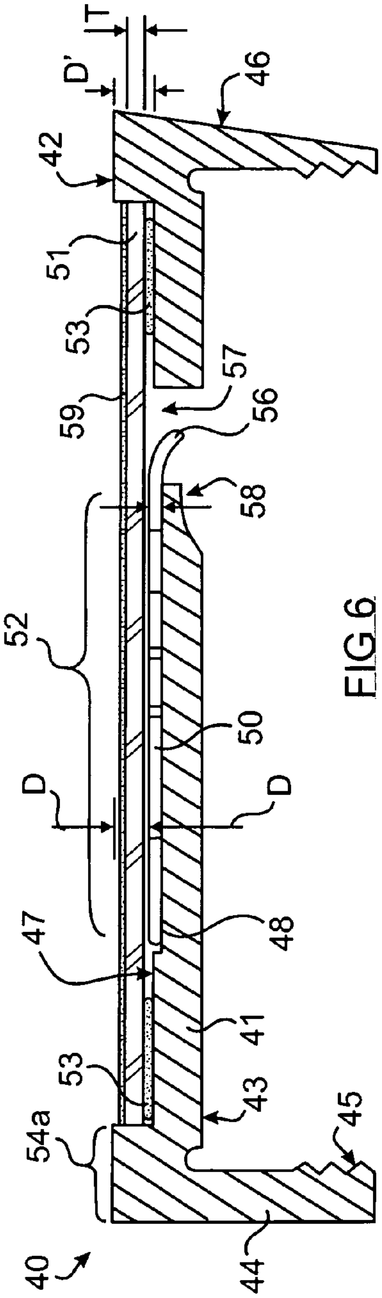
FIG. 6 is a cross-sectional view of the lid portion of the device of FIG. 5 taken along line 6-6.
Figure 5:
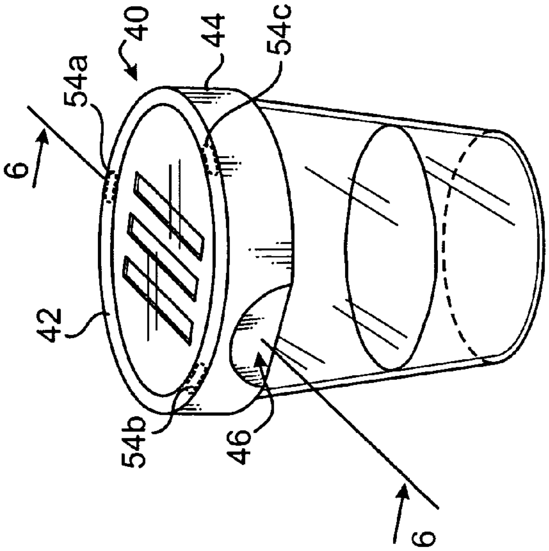
FIG. 5 is a perspective view of a second embodiment of a fluid-specimen device according to the invention in an upright orientation.

In FIGS. 5 and 6 there is shown an alternate embodiment of the device wherein the lid 40 has a generally disk-shaped top portion 41 having an outer, upper surface 42 and inner, lower surface 43. A substantially cylindrical flange 44 extends downward from the periphery of the top portion having inner threads 45 for attaching to the cup. The lid is generally formed from any type of rigid, durable, fluid impermeable and non-reactive material such as plastic. Unlike the previous embodiment, the material need not be transparent. In this embodiment a roll-inhibiting indentation 46 is set radially into a portion of the outer surface of the flange.

A generally disc-shaped valley 47 is formed into the outer surface of the lid. A channel 48 is formed into the bottom surface of the valley for each strip 50 to be carried by the lid. A generally disc-shaped transparent plate 51 fills the valley and covers the channels to form an individual pocket and a viewing window 52 for each strip. A layer of adhesive 53 or other means bond the plate to the bottom surface of the valley. The remaining peripheral ring of the upper surface 42 provides three upper spaced apart portions 54*a*, 54*b*, 54*c* which form a plane and tripod support for the device in the inverted orientation. Therefore, the thickness T of the plate is less than the depth D' of the valley so as to not interfere with the spaced apart portions. Again, the minimum distance D between the test strip and a scanner or photocopier contact surface is minimized so that precise recordation is accomplished.

As with the previous embodiment, the pocket formed by each covered oblong channel is sized and shaped to envelop the strip and allow for a aperture 55 through which extends the sampling pad portion 56 of the strip 50. A depression 57 is sized and shaped to enhance uniformity of exposure between the sampling pad 56 and the specimen by allowing controlled contact to both sides of the sampling pad. A divot 58 having a generally rounded shape and smooth surface is formed into the inner surface of the lid adjacent to the depression to further allow for the escape of air bubbles when the device is tipped into the tilted test orientation.

Optionally, the upper surface of the plate 51 is coated with a layer 59 of anti-reflective chemical coating material to reduce reflected light by about 98 percent, and hydrophobic material to lessen finger smudges thereby enhancing accurate recordation by reducing unwanted reflection and blurring. Such coatings are available from DENTON VACUUM, INC., of Moorestown, N.J. Alternately, other means such as lightly sanded upper surface may be used to reduce unwanted reflections.

Figure 7:
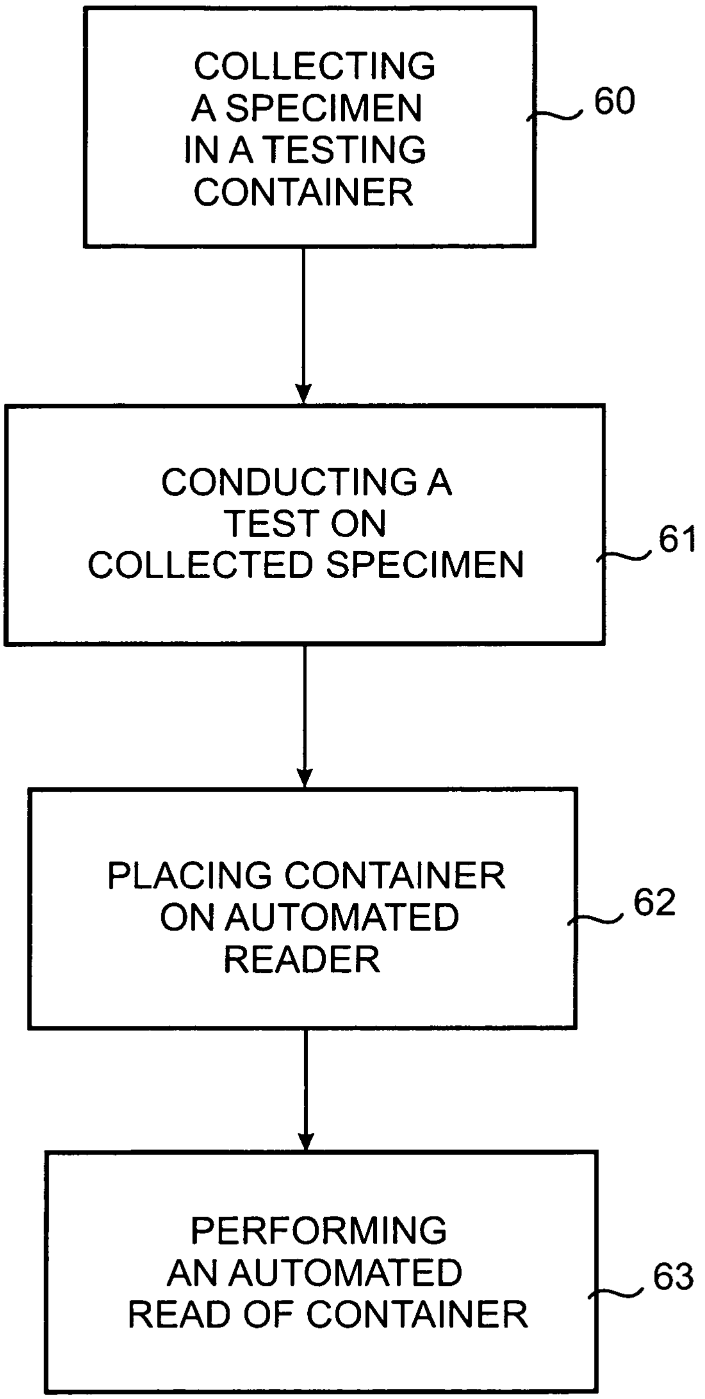
FIG. 7 is a flow-chart showing the method for recording a chromatographic assay test.

FIG. 7 is a flow-chart diagram demonstrating the preferred method for conducting an immunological assay test and making a permanent record of the results by photocopying the external surface of the lid. A fluid-specimen is collected 60 in a container by removing the lid, placing the specimen in the jar portion, and replacing the lid. A test is then conducted 61 by tipping the container to a predetermined angle whereby the fluid-specimen is allowed to contact a testing strip carried in the lid. The test is preferably conducted by merely placing the container in a tilted orientation on a flat surface so that a roll-inhibiting means stabilize the container, and waiting for a period of time sufficient to allow the test results to appear. Once testing is complete, the container is placed 62 in an orientation readable by an automated reading device. If the reader is a photocopier, the container is placed in an inverted orientation on the horizontal copier surface, the n performing 63 a read operation by taking a copy to create a permanent and objective record of the test results.

In this specification the term "transparent" means that the material will not significantly hamper the ability to read the results displayed or carried on the test strips.

Although the preferred embodiments disclose a generally cylindrical container, those skilled in the art will readily appreciate other non-cylindrically shaped containers or specimen carriers and lids which do not depart from the invention.

While the preferred embodiments of the invention have been described, modifications can be made and other embodiments may be devised without departing from the spirit of the invention and the scope of the appended claims.

What is claimed is:

1. A method for conducting a test of a liquid specimen, the method comprising:
- introducing the liquid specimen into a test device, the test device comprising an opening for receiving the liquid specimen and a lid for sealing the opening, the lid comprising:
  - at least one test strip carried on the lid;
  - an aperture exposing a portion of the at least one strip;
  - an arcuate peripheral flange; and,
  - roll-inhibiting ears extending from the flange;
- sealing the opening with the lid; and
- placing the test device in a stable tilted orientation roll-inhibitingly supported by the ears, thereby allowing an amount of said specimen to contact the at least one test strip through the aperture.

2. The method of claim 1, further comprising maintaining the at least one test strip in a substantially vertical orientation while the specimen test is conducted.

3. The method of claim 1, further comprising maintaining the test device in the stable tilted orientation using a roll-inhibiting indentation.

4. The method of claim 1, further comprising maintaining the test device in the stable tilted orientation using roll-inhibiting ears.

5. The method of claim 1, further comprising viewing the at least one test strip while the test device is in the stable tilted orientation.

6. The method of claim 1, the lid further comprising a transparent viewing window for viewing the at least one test strip.

7. The method of claim 6, wherein the at least one test strip is located adjacent to the transparent viewing window.

8. The method of claim 7, wherein the at least one test strip is located within at least one channel, the at least one channel being located on an interior surface of the lid.

9. The method of claim 8, wherein the at least one channel further comprises the aperture.

10. The method of claim 9, wherein the portion of the at least one test strip extends through the aperture.

11. The method of claim 10, further comprising allowing an amount of said specimen to contact the at least one test strip through the aperture.

12. The method of claim 1, wherein the at least one test strip is visible while the test device is in the stable tilted orientation.

* * * * *